US005522398A

United States Patent [19]

Goldenberg et al.

[11] Patent Number: 5,522,398
[45] Date of Patent: Jun. 4, 1996

[54] BONE MARROW BIOPSY NEEDLE

[75] Inventors: Alec Goldenberg, New York, N.Y.; Melvin R. Hoagland, III, So. Acton, Mass.

[73] Assignee: Medsol Corp., New York, N.Y.

[21] Appl. No.: 178,576

[22] Filed: Jan. 7, 1994

[51] Int. Cl.$^6$ ..................................................... A61B 10/00
[52] U.S. Cl. .............................................. 128/754; 128/749
[58] Field of Search ................................. 128/749, 751, 128/753, 754, 757; 606/167, 170

[56] References Cited

U.S. PATENT DOCUMENTS

| | | | |
|---|---|---|---|
| 3,605,721 | 9/1971 | Hallac | 128/2 B |
| 3,990,451 | 11/1976 | Gibbs | 128/305 |
| 4,258,722 | 3/1981 | Sessions et al. | 128/753 |
| 4,262,676 | 4/1981 | Jamshidi | 128/753 |
| 4,266,555 | 5/1981 | Jamshidi | 128/753 |
| 4,315,511 | 2/1982 | Chin | 128/305 |
| 4,356,828 | 11/1982 | Jamshidi | 128/754 |
| 4,461,305 | 7/1984 | Cibley | 128/754 |
| 4,576,162 | 3/1986 | McCorkle | 128/303 |
| 4,651,752 | 3/1987 | Fuerst | 128/754 |
| 4,653,496 | 3/1987 | Bundy et al. | 128/305 |
| 4,745,919 | 5/1988 | Bundy et al. | 128/305 |
| 4,785,826 | 11/1988 | Ward | 128/754 |
| 4,798,213 | 1/1989 | Doppelt | 128/754 |
| 4,881,550 | 11/1989 | Kothe | 128/752 |
| 4,926,877 | 5/1990 | Bookwalter | 128/754 |
| 4,932,417 | 6/1990 | Ott | 128/757 X |
| 4,935,025 | 6/1990 | Bundy et al. | 606/180 |
| 5,005,585 | 4/1991 | Mazza | 128/754 |
| 5,040,542 | 8/1991 | Gray | 128/754 |
| 5,074,311 | 12/1991 | Hasson | 128/754 |
| 5,133,360 | 7/1992 | Spears | 128/754 |
| 5,148,813 | 9/1992 | Bucalo | 128/754 |
| 5,267,572 | 12/1993 | Bucalo | 128/754 |
| 5,271,414 | 12/1993 | Partika et al. | 128/754 |

Primary Examiner—Sam Rimell
Attorney, Agent, or Firm—Darby & Darby

[57] ABSTRACT

An improved biopsy needle having an outer cannula, an inner tube and a stylet. The distal end of the inner tube is provided with a snare in the form of a coil extending from the inner tube. The free end of the coil is adhered to the inner surface of the outer cannula. Upon rotation of the inner tube with respect to the outer cannula, the coil will decrease in diameter to either sever or hold the biopsy piece within the outer needle. After removal of the needle from the patient, rotating the inner tube in the opposite direction will cause the coil to expand to its original diameter and allow the biopsy piece to be removed from the needle.

14 Claims, 4 Drawing Sheets

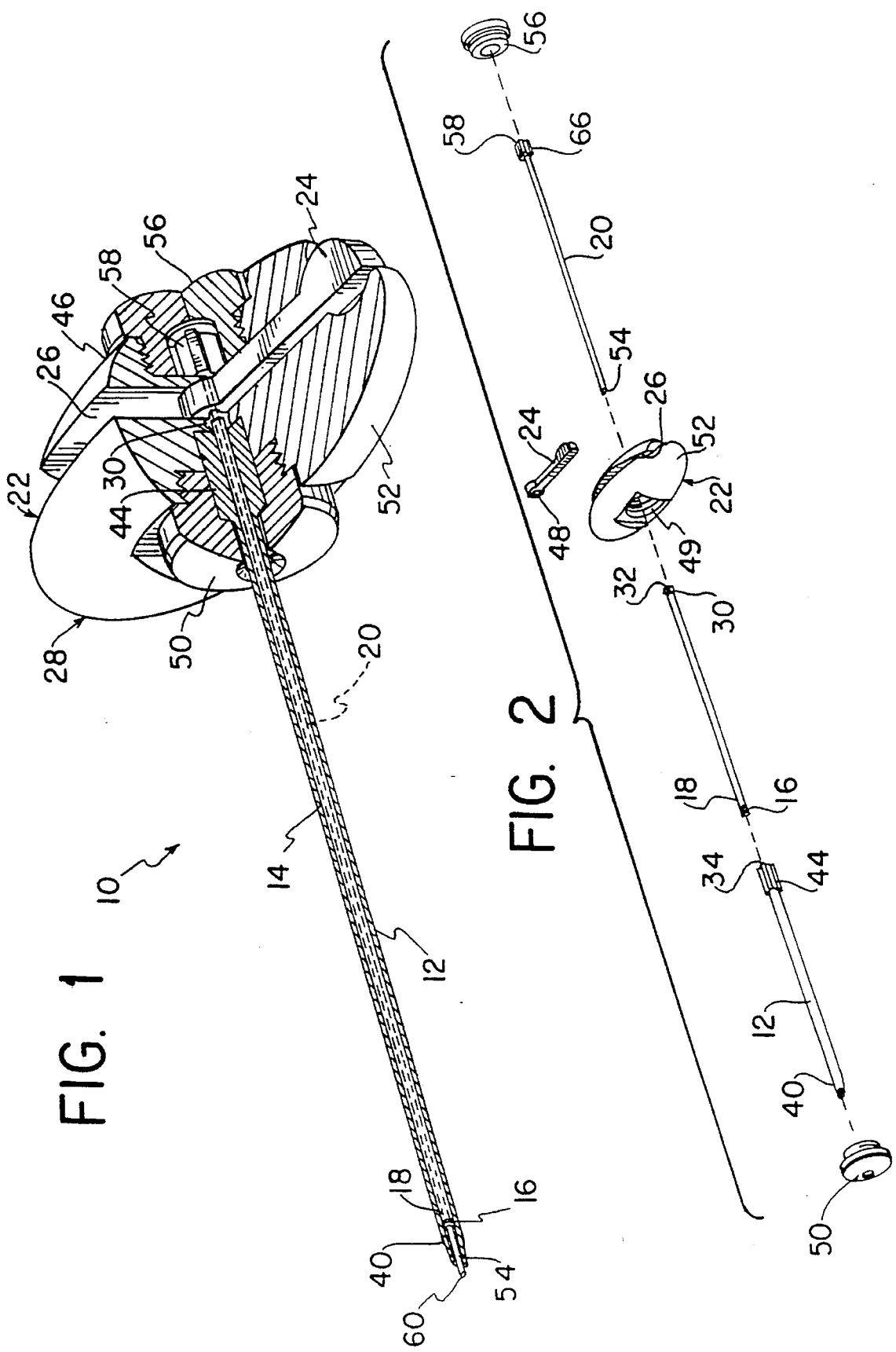

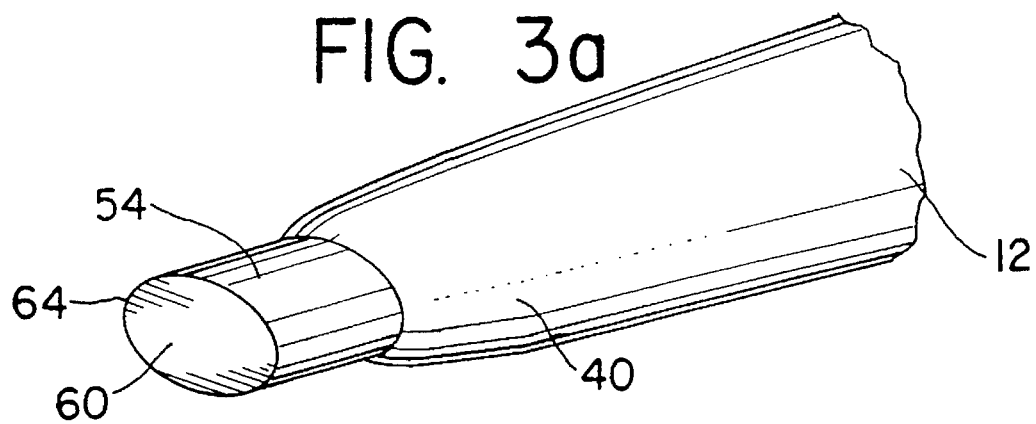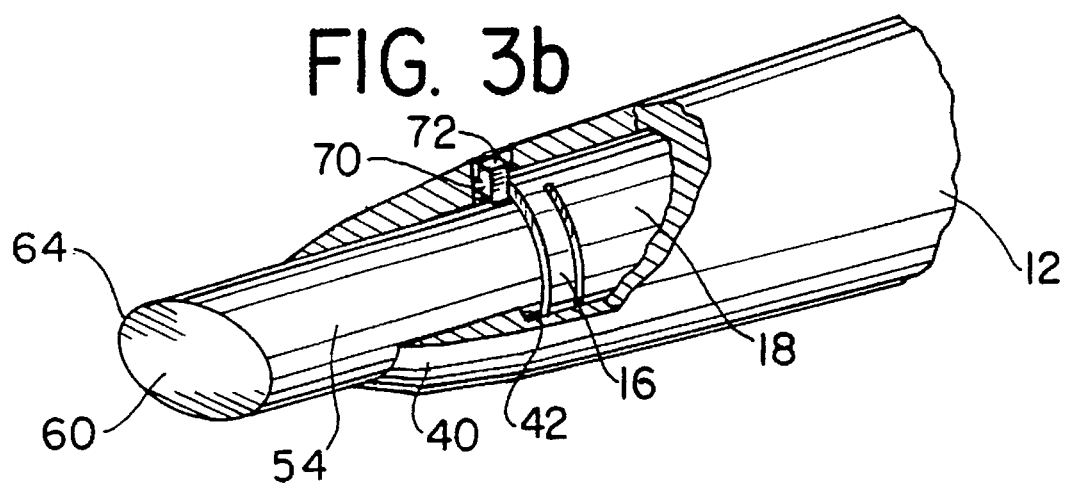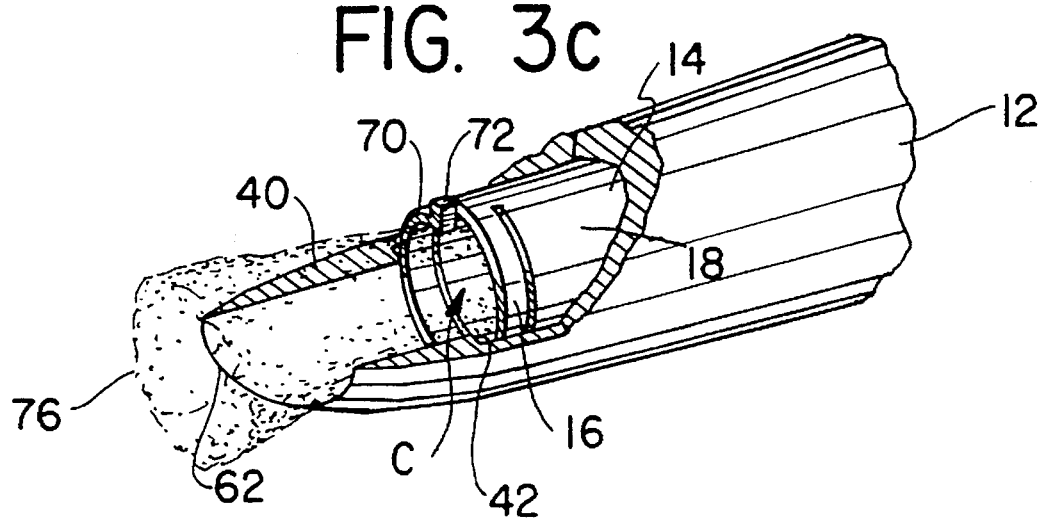

BONE MARROW BIOPSY NEEDLE

FIELD OF THE INVENTION

This invention relates generally to a surgical instrument, known variously as a biopsy needle or cannula that is used to gather tissue, such as bone narrow, from living persons or animals for pathological study. More specifically, the invention relates to a biopsy needle having an improved structure for severing a tissue sample and/or retaining the tissue sample within the needle.

BACKGROUND OF THE INVENTION

For various medical reasons, such as diagnostic tests or the determination of suitability as a tissue donor, it is often necessary for a physician to obtain a sample of a patient's body tissue. In particular, bone marrow is frequently retrieved for later pathological study. The current procedures and instruments used for obtaining the samples, while not overly complex, almost universally result in excessive patient discomfort and often overly extends the patient's and operator's time, money and effort. In the standard bone marrow procurement protocol, using currently standard instruments, (such as those disclosed in U.S. Pat. No. 4,262,676 to Khosrow Jamshidi), the patient is prepared with a suitable local anesthetic at the appropriate marrow retrieval site. Then, a relatively narrow needle is inserted to obtain an aspirate of only liquid bone marrow material for making slides for examination after staining. This portion of the procedure referred to as the bone marrow aspiration, is relatively less painful than obtaining a bone marrow biopsy.

After the aspirate is obtained and the slides and specimens are prepared, if necessary, a biopsy of the fibrous bone marrow is taken. A significantly wider bore needle having an inner diameter that will house a suitable marrow sample is first prepared with an inner stylet that extends beyond the distal end of the outer needle. The stylet distal end may be cut at an angle, with the leading edge sufficiently sharp to pierce tissue and bone. With the stylet in place within the outer needle, the needle is pushed through the outer layers of flesh until the bone is felt at the tip. The needle and styler are then pushed into the bone approximately 4 or 5 millimeters until the needle appears to be solidly within the bone.

The stylet is then removed from the proximal end of the needle, which opens up the core of the needle to the now-surrounding marrow tissue. The outer needle is then usually advanced another 1 to 2 centimeters at minimum with a slight twisting motion. Often, the distal end of the outer needle will also be provided with an angled cut and sharpened leading edge to easily cut and core the tissue. By providing a slight twisting motion as the needle is advanced, usually with no more than quarter or half turns, an appropriate sample is cored from the marrow tissue and enters the inner passage of the marrow needle.

At this point, the marrow biopsy sample piece is ready to be removed from the patient, although it is important that the biopsy piece remain within the needle as the needle is withdrawn. If the biopsy piece becomes dislodged and falls out the distal end of the biopsy needle, the piece is irretrievably lost. The procedure is then unsuccessful and must be repeated from the beginning.

Various methods have been attempted by physicians to prevent the biopsy piece from dislodging from the outer needle. For example, some physicians, after the needle has entered the bone fully and cored a sample from the marrow, will pull the biopsy needle back a few millimeters and then forward a few millimeters at a different angle than the first insertion. This theoretically will "cut" the biopsy piece at the tip of the needle. Other physicians attempt to dislodge or disrupt the connection between the biopsy piece and the bone by making multiple complete clockwise and counter-clockwise rotations of the biopsy needles while within the bone. Some physicians even hit the proximal end of the biopsy needle at its handle in an attempt to mechanically disrupt the connection between the core biopsy specimen and the additional bone.

As can be plainly realized, these manipulations at the end of the procedure, attempts at ensuring that the biopsy piece remains within the needle, can often produce substantial discomfort and anxiety. Sometimes when the bone marrow is very soft, as in patients with osteoporosis, almost all of these attempts are futile because the bone structure is so fragile. Conversely, sometimes when the bone marrow is very fibrotic, which occurs in patients with myelofibrotic diseases or in AIDS patients, it is difficult to dislodge the core biopsy piece, since the bone marrow itself is reinforced by surrounding tissue. In those cases, the cored biopsy piece often remains attached to the bone and is not removed in the biopsy process.

Other attempts at designing a more efficient and successful biopsy needle have met with little or no success, for various reasons, including the complexity of the devices. For example, U.S. Pat. No. 3,605,721 to Hallac, discloses a biopsy needle in which an inner tube has a weakened portion represented by strips extending between distal and proximal portions of the inner tube. The distal portion of the inner tube is adhered to an outer tube and will not rotate. Once a biopsy piece has entered the needle, the proximal portion of the inner tube is rotated, causing the strips to twist together and eventually break off. This twisting motion tends to twist the strips to the tube's center, thus hopefully keeping the biopsy piece proximal of the twisted and broken strips for later removal. This particular biopsy needle is only a disposable device, since the strips are broken or irreversibly warped by plastic deformation during the twisting process. Another disadvantage is the lack of control over the twisting motions or the breakage of the strips. Essentially, the surgeon is left to twist the inner tube until resistance to that twisting is lost, indicating that the strips have severed. There is also no way of releasing the device's grip on tissue during surgery, should any problems arise.

U.S. Pat. No. 5,074,311 to Hasson discloses a biopsy device that includes a pair of inner jaws that can be actuated within the outer needle to "bite off" any biopsy piece that has entered the outer needle. The disadvantages of this device include multiple small mechanical linkages and parts including pivot pins, which are extremely difficult and expensive to assemble and maintain, in addition to the greatly increased chance of mechanical failure which can be costly during a surgical procedure.

SUMMARY OF THE INVENTION

In view of the deficiencies noted in the prior references and the current protocols, it is an object of the present invention to provide an improved biopsy needle that will sever a tissue sample from surrounding tissue or hold it with sufficient force such that the action of removing the needle detaches the piece from the surrounding tissue.

It is another object of the invention to provide a biopsy needle that requires minimal manipulation of the needle at the end of the procedure, thus decreasing patient pain and anxiety.

It is a further object of the invention to ensure obtaining a biopsy sample with each attempt, thus decreasing the number of necessary biopsy attempts, and the time, effort and money expended on the overall procedure.

It is yet another object of the invention to provide a biopsy needle that is simple and inexpensive to manufacture, may be reusable, and is simple to operate.

According to the objects of the invention, an improved biopsy needle has an outer cannula, an inner tube and a stylet. The distal end of the inner tube is provided with a snare in the form of a coil extending from the inner tube. The free end of the coil is adhered to the inner surface of the outer cannula. Upon rotation of the inner tube with respect to the outer cannula, the coil will decrease in diameter to either sever or hold the biopsy piece within the outer needle. After removal of the needle from the patient, rotating the inner tube in the opposite direction will cause the coil to expand to its original diameter and allow the biopsy piece to be removed from the needle.

BRIEF DESCRIPTION OF THE DRAWINGS

Other objects, advantages and embodiments than those described above will become apparent to those skilled in the art upon reading the following detailed description of the preferred embodiments in conjunction with a review of the appended drawings, in which:

FIG. 1 is a perspective view of a biopsy needle in accordance with the present invention;

FIG. 2 is an exploded view of the biopsy needle according to the present invention;

FIGS. 3a–3e are detail perspective views of the distal ends of various components during operation of the biopsy needle;

DETAILED DESCRIPTION OF THE PREFERRED EMBODIMENTS

Figure 3D:
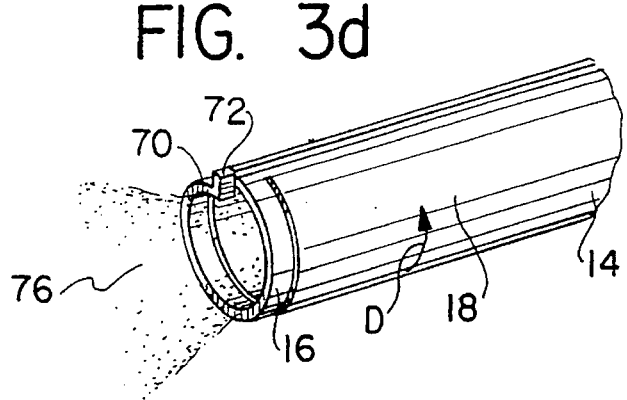

Referring now to FIGS. 1 and 2, a biopsy needle 10 has an outer cannula 12, an inner tube 14 with a snare 16 at its distal end 18, a stylet 20, and a handle assembly 22. In FIG. 2, the assembly of the present biopsy needle 10 is shown in an exploded view.

Figure 4:
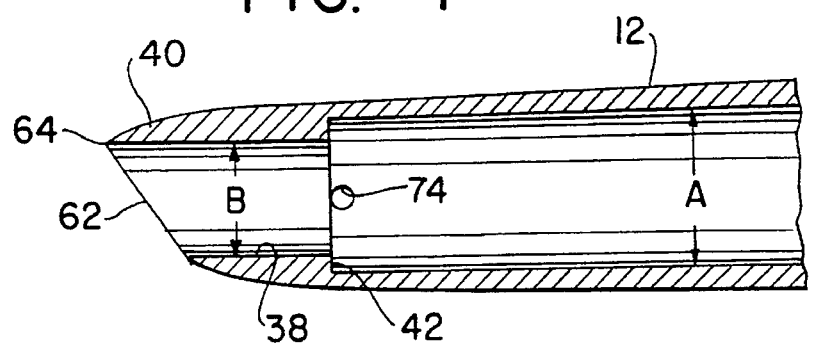
FIG. 4 is a cross-section of the distal end of the outer cannula.

As part of the handle assembly 22, a lever 24 fits into a corresponding groove 26 within a handle piece 28. The lever 24 actuates the snare 16 within the outer cannula 12 without any movement of the outer cannula 12 relative to the patient (not shown). The functioning of this lever 24 is described more fully below. The inner tube 14 has a snare 16 at its distal end 18 and a gear 30 mounted on its proximal end 32. The inner tube 14 is inserted into the proximal end 34 of the outer cannula 12 with the gear 30 extending out of the proximal end 34. As can be seen in FIG. 4, the interior of the outer cannula 12 has a constant inner diameter A along a majority of its length, with a portion 38 having a smaller inner diameter B at its distal tip 40.

Preferably, the narrow inner diameter B at the distal tip 40 is substantially equal to the inner diameter C of the inner tube 14 so that there will be no ridge or lip within the instrument to impede tissue entering the instrument. The inner tube 14 is inserted until the snare 16 reaches the shoulder 42 provided on the interior of the outer cannula 12 at the position where the diameter changes.

With the gear 30 extending proximal of the cannula's anchor 44, the cannula and snare assembly are attached to the handle piece 28 at the proximal facing side 46 of the handle 22. The gear 30 of the snare 16 is inserted into a complementary hole 48 in the lever while the anchor 44 of the outer cannula 12 mates with a complementary hole 49 in the handle piece 28. Thus, when the lever 24 is rotated within its groove 26 with respect to the handle piece 28, the inner tube 14 will rotate with respect to the outer cannula 12. A cannula cap 50 is assembled onto the distal tip 40 of the cannula and threadedly engaged to the forward facing end 52 of the handle piece 28. The stylet 20 is inserted into the proximal end 32 of the inner tube until a distal tip portion 54 of the stylet extends beyond the distal tip 40 of the cannula. A stylet cap 56 can then be threadedly engaged to the proximal facing side 46 of the handle piece, covering the proximal end 58 of the stylet to prevent it from moving proximally within the inner tube 14.

As can be seen in FIG. 3a, both the distal ends 40, 54 of the stylet and the outer cannula preferably have sloped end faces 60, 62 although it is not necessary. This improves the cutting actions of the both the stylet and the outer cannula by providing sharp leading edges 64. In this position, the stop 66 at the proximal end 58 of the stylet preferably mates with a complementary indent 68 in the handle piece 28 to maintain the rotational orientation of the stylet 20 with respect to the outer cannula 12 such that the slopes of the two distal ends 40, 54 are approximately parallel. This is the configuration that would be used for inserting the biopsy needle 10 into the patient and through the bone into the softer bone marrow tissue within.

As can be seen in FIG. 3b, which is a partial cutaway view, the free end 70 of the coil snare 16 includes a tab 72 that engages or is attached to a hole 74 (FIG. 4) on the interior surface of the outer cannula 12. This hole 74 preferably extends through the entire wall of the outer cannula. If desired, the tab 72 can be adhered to the hole 74 in the outer cannula through the use of adhesives, welding, or any known attachment process. After the needle 10 is inserted into the marrow, the stylet 20 is removed proximally without any movement of the outer cannula 12 with respect to the patient, minimizing discomfort. As can be seen in FIG. 3c, marrow tissue may now enter the passageway within the outer cannula 12 through the distal end 40 of the outer cannula and can enter the inner passageway of the inner tube 14, preferably to a position proximal of the snare 16.

Figure 3E:
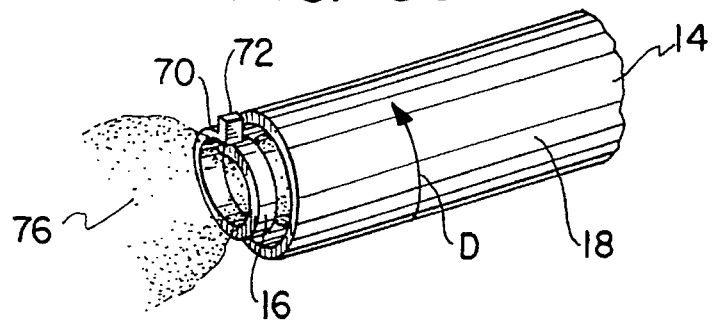

To operate the snare 16, i.e. to cause cutting and/or holding of the biopsy piece 76 within the inner tube 14, the lever 24 attached to the proximal end 32 of the inner tube is rotated in the direction of arrow D as seen in FIGS. 3d–3e. Of course, the snare 16 can be designed such that rotation in the opposite direction causes the same effect. With full rotation (180°) of the lever 24, the inner tube 14 and snare 16 achieve a position similar to that shown in FIG. 3e, in which the inner tube 14 has been rotated approximately 180°. Since the free end 70 of the snare is fixed to the outer cannula 12, the result of the rotation is that the coil of the snare 16 will tighten so that the cross-sectional area through the snare 16 is approximately less than a third of the area when in the open configuration. It is also contemplated that any decrease, even a slight decrease, in the cross-sectional area of the snare will cause pressure on the biopsy piece 76. Therefore, while the current amount of rotation is preferred, it is not necessary for the proper functioning of the present invention.

Figure 5:
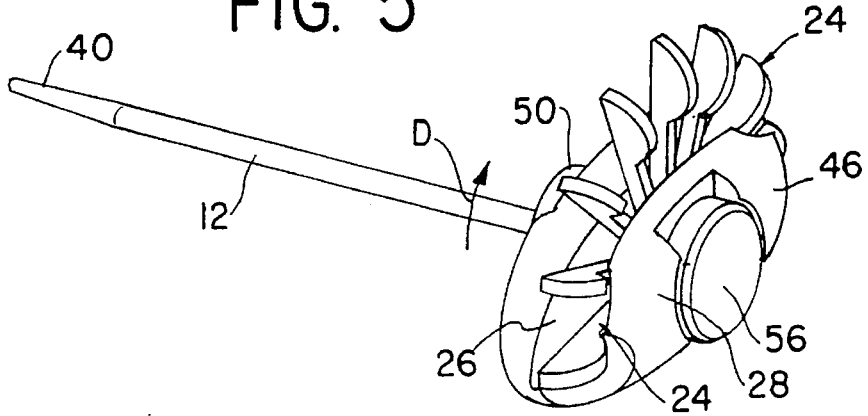
FIG. 5 is a perspective view of the biopsy needle showing operation by a physician.
Figure 6:
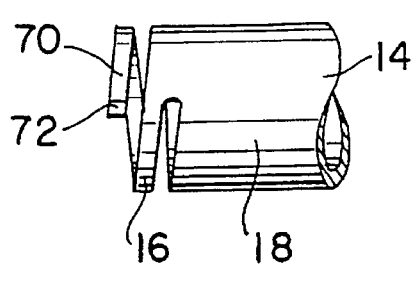
FIG. 6 is a detail side view of the inner tube of the present invention.

As seen in FIG. 5, movement of the lever 24 can be independent of any movement of the handle piece 28 or the outer cannula 12. Therefore, the outer cannula 12, which is in direct contact with the patient while the sample is taken, can remain substantially stationary. There is little or no discomfort at this step of the procedure, where previously this had been one of the more uncomfortable steps.

With the tightening of the snare 16, there is a high probability that the biopsy piece 76 will remain in the needle 10 as the needle is removed. If the tightening of the snare 16 does not immediately cause the biopsy piece 76 to be cut, it will be significantly squeezed and/or notched, such that rearward motion of the needle 10, which causes rearward pressure on any biopsy piece 76 proximal of the snare 16, will cause material proximal of the snare 16 to detach from material that is distal of the snare.

Figure 7:
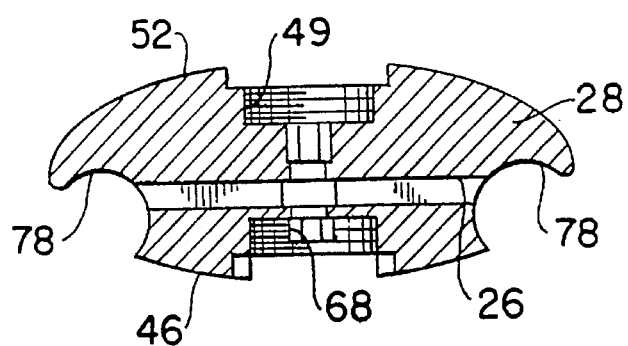
FIG. 7 is a cross-section view through the handle piece of the biopsy needle.

As can be seen in FIG. 7, the handle 22 includes several features designed for ease of use of the physician and ease of manufacture and construction. The handle piece 28 includes a groove 26 that holds the lever 24. The groove 26 has two notches 78 that generally protect the lever 24 from any accidental contact with the physician when in either the full-open or full-closed positions, but allow access to the lever. Further, the holes in the handle piece 28 that receive the anchor 44 of the outer cannula and the stop 66 of the stylet have complementary shapes in order to prevent rotation of those two components with respect to the handle, as previously discussed. The proximal and distal facing sides 46, 52 of the handle piece are also provided with threaded regions for receiving the cannula and stylet caps 50, 56.

Once the biopsy needle 10 has been used and the captured material has been ejected through either the proximal or distal ends of the inner tube, the biopsy needle 10 is then ready to be sterilized for its next use. If necessary, the entire biopsy needle can be disassembled, although the tab 72 at the free end of the snare must be disengaged from the hole 74 in the outer cannula. This can be accomplished with any small tool pushed through hole 74. If the free end 70 of the snare is permanently adhered to the outer cannula 12, it then may be necessary to sterilize the outer cannula and inner tube as a single unit. However, due to the few number of parts and relative ease and low cost construction of the present needle, it is also contemplated that such a device is easily disposable.

Thus, it can be seen that a low cost, simply-manufactured biopsy needle will attain improved results over known devices, not only in the success rate of the marrow extraction procedures, but also a marked increase in patient comfort throughout the procedure. One desirable side benefit of this increased comfort might be increased participation in bone marrow donor programs for transplant candidates.

While the embodiments shown and described above are fully capable of achieving the objects and advantages of the present invention, it is to be understood that these embodiments are shown and described solely for the purposes of illustration and not for limitation.

What is claimed is:

1. A biopsy needle for removal of tissue from a patient, comprising:

an outer tube having a proximal and a distal end;

an inner tube within said outer tube, said inner tube having a proximal and a distal end;

a snare having two ends, one of said ends connected to said inner tube and the other of said ends coupled to said outer tube, said snare having a first and a second position, wherein in said first position, said snare has a first diameter and wherein in said second position, said snare has a second diameter smaller than said first diameter, said snare being moved from said first position to said second position by rotation of said inner tube with respect to said outer tube in one direction and being moved from said second position to said first position by rotation in an opposite direction.

2. A biopsy needle as in claim 1, wherein said snare is a helical coil.

3. A biopsy needle as in claim 2, wherein said coil is integral with said inner tube.

4. A biopsy needle as in claim 3, further comprising a stylet within said inner tube, said stylet extending beyond said distal end of said outer tube.

5. A biopsy needle as in claim 4, wherein said stylet has a distal end, said distal ends of said stylet and said outer tube being sloped with respect to a transverse direction.

6. A biopsy needle as in claim 2, further comprising a handle, said handle being attached to said proximal end of said outer tube, said handle having a lever, said lever being attached to said proximal end of said inner tube such that movement of said lever causes rotation of said inner tube.

7. A reusable biopsy needle, comprising:

an outer tube;

an inner tube within said outer tube, said inner tube having means for holding the biopsy sample with a force sufficient to detach the biopsy sample from surrounding tissue when the biopsy needle is withdrawn, said means extending within said outer tube and having one portion connected to said inner tube and another portion coupled to said outer tube, said means being elastically deformable so that the biopsy needle can be reused without withdrawing the biopsy needle.

8. A biopsy needle as in claim 7, further comprising a means for rotating said inner tube with respect to said outer tube.

9. A biopsy needle as in claim 8, further comprising a handle irrotatably engaged to said outer tube, said handle having said means for rotating said inner tube mounted thereon.

10. A biopsy needle as in claim 9, wherein said outer tube has a first inner diameter over a first portion thereof and a second inner diameter smaller than said first inner diameter over a second portion thereof, said first inner diameter being dimensioned to accommodate said inner tube.

11. A biopsy needle as in claim 10, wherein said outer tube has a distal end, said second portion being at said distal end.

12. A biopsy needle as in claim 7, further comprising means for selectively attaching and detaching said inner and outer tubes.

13. A biopsy needle as in claim 12, wherein said means for selectively attaching and detaching said inner and outer tubes comprises a tab on one of said inner and outer tubes, the other of said inner and outer tubes having a hole.

14. A biopsy needle as in claim 13, wherein said hole is in said outer tube.

* * * * *